United States Patent
Burnette et al.

(10) Patent No.: US 7,290,447 B1
(45) Date of Patent: Nov. 6, 2007

(54) DENSITY MEASURING APPARATUS CONTAINING A DENSIMETER AND A METHOD OF USING THE SAME IN A PIPELINE

(75) Inventors: Blake Burnette, Spring, TX (US); Bradley T. Carlson, Cypress, TX (US); Don Wade, Montgomery, TX (US)

(73) Assignee: BJ Services Company, Houston, TX (US)

( * ) Notice: Subject to any disclaimer, the term of this patent is extended or adjusted under 35 U.S.C. 154(b) by 0 days.

(21) Appl. No.: 10/680,306

(22) Filed: Oct. 7, 2003

(51) Int. Cl.
*G01N 9/02* (2006.01)

(52) U.S. Cl. .......................................... 73/433; 73/434

(58) Field of Classification Search ................. 73/433, 73/434
See application file for complete search history.

(56) References Cited

U.S. PATENT DOCUMENTS

| | | | | |
|---|---|---|---|---|
| 1,905,558 A | * | 4/1933 | Foote | 73/861.69 |
| 2,613,530 A | * | 10/1952 | Nichols | 73/434 |
| 2,669,118 A | * | 2/1954 | Nichols | 73/434 |
| 3,143,887 A | * | 8/1964 | Hathorn et al. | 73/434 |
| 3,320,791 A | * | 5/1967 | Banks | 73/32 A |
| 3,503,267 A | * | 3/1970 | Shiba et al. | 73/434 |
| 4,285,239 A | * | 8/1981 | Heine et al. | 73/434 |
| 4,510,808 A | | 4/1985 | Neville | |
| 4,745,807 A | | 5/1988 | O'Neill | |
| 4,817,428 A | | 4/1989 | Ford et al. | |
| 4,856,347 A | | 8/1989 | Johnson | |
| 5,571,281 A | * | 11/1996 | Allen | 366/2 |
| 6,007,227 A | | 12/1999 | Carlson | |
| 6,210,727 B1 | | 4/2001 | Miller et al. | |
| 6,491,421 B2 | * | 12/2002 | Rondeau et al. | 366/8 |
| 6,581,451 B2 | * | 6/2003 | Ence et al. | 73/149 |
| 7,056,008 B2 | * | 6/2006 | Rondeau et al. | 366/8 |
| 2002/0093875 A1 | * | 7/2002 | Rondeau et al. | 366/8 |

FOREIGN PATENT DOCUMENTS

WO    WO 200244517 A1 *  6/2002

* cited by examiner

*Primary Examiner*—Hezron Williams
*Assistant Examiner*—Samir M. Shah
(74) *Attorney, Agent, or Firm*—Locke Liddell & Sapp PLLC

(57) ABSTRACT

A densimeter contains an inlet pipe section, a second pipe section joined to the downstream end of the inlet pipe section, and an outlet pipe section joined to the downstream end of the second pipe section. The inlet and outlet pipe sections are constrained by a support structure, while flexible couplings allow the second section of pipe to undergo a limited amount of radial motion relative to the adjacent pipe sections. The weight of the second pipe section is supported by a weight measuring unit, which continuously measures the weight of the second pipe section as fluid flows through the densimeter. One preferred embodiment of the invention uses the densimeter to measure the density of a proppant in a blender system for preparing fluid mixtures for fracturing and propping oil bearing geological formations.

18 Claims, 4 Drawing Sheets

DENSITY MEASURING APPARATUS CONTAINING A DENSIMETER AND A METHOD OF USING THE SAME IN A PIPELINE

FIELD OF THE INVENTION

The present invention relates generally to a density measuring apparatus for measuring the density of a fluid flowing continuously through a pipeline, and a method of using the same. In a preferred embodiment, the density measuring apparatus of the invention is used to measure the density of a proppant slurry in a blender system for preparing fluid mixtures for fracturing and propping oil bearing geological formations.

BACKGROUND OF THE INVENTION

Fracturing and propping an oil well is a well known process in which fluid, generally water or oil, is pumped into an oil well at high flow rates (typically 200 to 5000 gallons per minute) and high pressures to hydraulically fracture the underlying oil bearing formation. The fluid is combined with any number of chemicals to produce certain fluid properties. Generally the fluid is mixed with certain polymers to increase its viscosity and allow it to transport a proppant into the fracture created. The fluid is further designed to lose viscosity once it is in the fracture allowing it to leave the porous proppant in the fracture to provide a path for the oil to flow back to the well bore.

To achieve the best performance from the fluid, the various components of the fluid must be mixed together in the proper proportions. One way to verify the composition of the fluid is to measure its density. Because the various components have different densities, the density of the fluid will vary according to the composition of the fluid. It is desirable to measure the density of the fluid before the fluid leaves the blender system, so that the composition of the fluid can be corrected before the fluid is pumped into the well.

Several different types of densimeters are currently used to measure the density of the fluid in the blender system. Some densimeters known in the art use a nuclear gauge which sends a stream of gamma rays through the flowing fluid and determines the density based on the amount of radiation scattered by the fluid. These nuclear densimeters have certain drawbacks, including safety concerns that are always present when working with radioactive materials, and a time lag associated with each density measurement. Also, nuclear densimeters measure the density of only a localized area of the fluid. This is a disadvantage when using a fluid such as a sand slurry, that may not have uniform consistency. When using a nuclear densimeter with such a fluid, the densimeter may measure a localized change in density due to a small pocket of denser material that is not thoroughly mixed into the surrounding fluid. In that case, it is impossible to know whether the changed density is due to a localized concentration of material or a systemic problem with the fluid composition.

Another method of measuring fluid density involves diverting a portion of the fluid flow into a separate U-tube. The U-tube is weighed, along with its contents. The density of the fluid is then calculated, based on the fluid volume contained in the U-tube. While eliminating the safety concerns associated with nuclear densimeters, U-tube densimeters can still provide misleading results when used with inconsistently mixed fluids. Furthermore, the additional tubing needed to construct the U-tube presents a disadvantage, especially in an oilfield environment.

It is the object of the present invention to provide an improved density measuring apparatus which is capable of accurately measuring the density of a fluid flowing in a pipeline and which is not nuclear based. More specifically, it is an object of the present invention to provide a densimeter that can measure the density of a sufficiently large sample of the fluid such that the effect of any local inconsistencies in the fluid composition on the density measurement is minimized. Additionally, it is an object of the present invention to provide a densimeter having a simple, durable structure. It is also an object of the invention to provide a densimeter which produces a density measurement with no appreciable time delay, so that any irregularities in the fluid composition can be identified and corrected immediately.

Further, it is the object of the present invention to provide a method of using the density measuring apparatus to measure the density of a fluid flowing in a pipeline. More specifically, it is an object of the present invention to provide a method of measuring the density of a fluid of unknown density flowing in a closed pipeline system, such as a cementing unit or a blender system for preparing fluid mixtures for fracturing and propping oil bearing geological formations.

SUMMARY OF THE INVENTION

The present invention provides an apparatus capable of continuously measuring the density of a fluid flowing through a pipeline. The apparatus of the present invention comprises an inlet pipe section, a second pipe section joined to the downstream end of the inlet pipe section, and an outlet pipe section joined to the downstream end of the second pipe section. The inlet and outlet pipe sections are constrained by a support structure as known in the art, but the flexible couplings allow the second section of pipe to undergo a limited amount of radial motion relative to the adjacent pipe sections. The weight of the second pipe section is supported by a weight measuring unit, such as a load cell, which continuously measures the weight of the second pipe section as fluid flows through that pipe section. In this way, the entire second pipe section functions as a densimeter.

For a pipe section having a known empty weight and a known fluid flow volume, the density of the fluid can be easily calculated based on the weight measured by the weight measuring unit. Because the sample size includes all of the fluid in the second pipe section, localized inconsistencies in the mixture are not reflected in the density measurement. Furthermore, the structure of the density measuring apparatus is simple and durable, making it easy to install and maintain in a variety of applications. Also, the weight measuring unit measures the weight of the second pipe section continuously, eliminating the time delay.

In one specific embodiment described herein, the apparatus of the invention is used to measure the density of a proppant in a blender system for preparing fluid mixtures for fracturing and propping oil bearing geological formations. The discharge manifold of the blender system is fitted with a flexible coupling on each end, permitting it a limited range of motion independent of the pipe sections immediately upstream and downstream. A load cell measures the weight of the discharge manifold during fluid flow.

The invention also encompasses an improved method for measuring the density of a fluid flowing through a closed pipeline system. According to the method of the invention, the densimeter is first calibrated by weighing the densimeter while a fluid of known density flows through the pipeline. Next, a fluid of unknown density is introduced into the pipeline. As the fluid flows through the densimeter, the combined weight of the densimeter and the fluid is measured. From this information, the density of the fluid is calculated.

DESCRIPTION OF THE DRAWINGS

In order to more fully understand the drawings referred to in the detailed description of the present invention, a brief explanation of each drawing is presented, in which.

DETAILED DESCRIPTION OF THE PREFERRED EMBODIMENT

Figure 1:
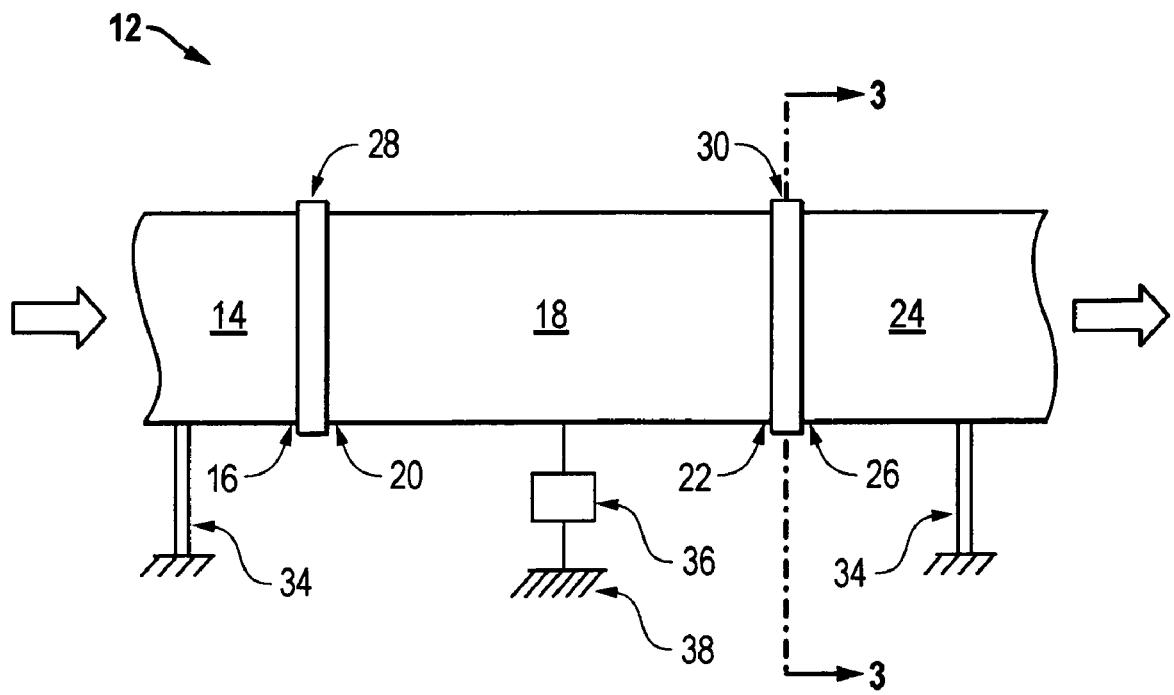
FIG. 1 is a schematic side view of a pipeline incorporating a densimeter according to the invention.
Figure 2:
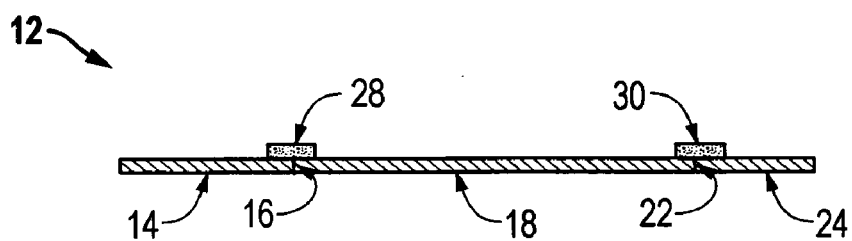
FIG. 2 is a cross-sectional schematic side view of the pipeline of FIG. 1, showing how the flexible couplings join adjacent pipe sections.
Figure 2:
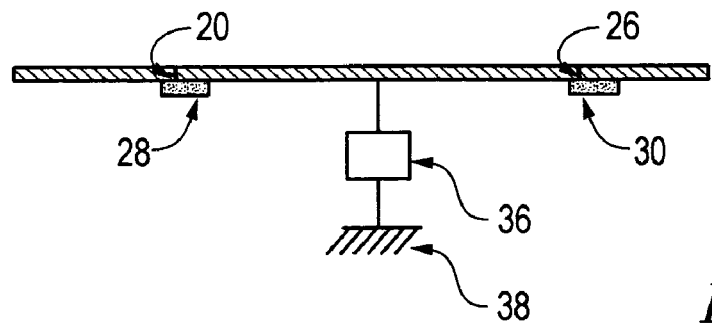
Figure 3:
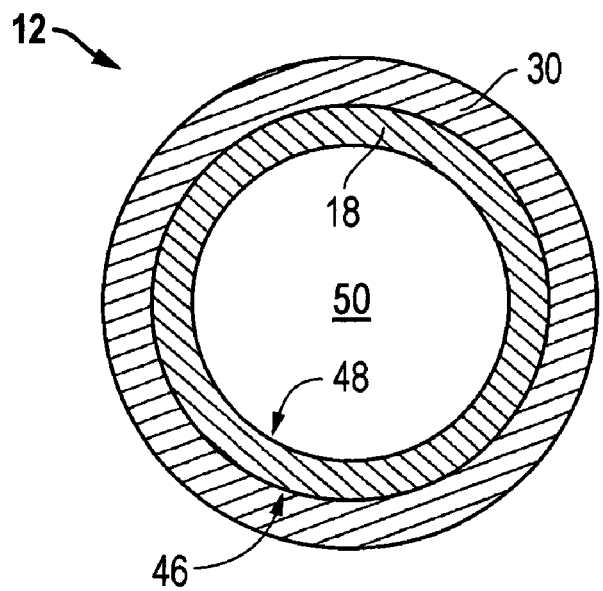
FIG. 3 is a cross-sectional schematic front view of the pipeline of FIG. 1, taken along the line 3-3 of FIG. 1.

FIGS. 1-3 have similar elements that are similarly numbered and will be described in conjunction with each other. A pipeline carries a fluid flow in the direction indicated by the arrows in FIG. 1. A densimeter 12 is installed in the pipeline, the densimeter 12 comprising an inlet section 14 having a downstream end 16, a second section 18 having an upstream end 20 and a downstream end 22, and an outlet section 24 having an upstream end 26. A first flexible coupling 28 joins the inlet section downstream end 16 to the second section upstream end 20. A second flexible coupling 30 joins the second section downstream end 22 to the outlet section upstream end 26. The flexible coupling may be any type of flexible connector known in the art, including, without limitation, elastomeric couplings or flexible metal couplings. A preferred embodiment uses part number 208-008 mechanical joint couplings manufactured by John L. Schultz, Ltd.

An inlet support 32 carries the weight of the inlet section 14, while an outlet support 34 carries the weight of the outlet section 24. A weight measuring unit 36 positioned underneath the second section 18 carries the weight of the second section 18. The weight measuring unit 36 also measures the weight of the second section 18 as fluid flows through the second section 18. In a preferred embodiment, the weight measuring unit 36 is a compression-type load cell, such as the LCH series manufactured by Omega Engineering. However, the densimeter will function equally well with any other type of weight measuring unit known to the art, such as a hydraulic gauge. The weight measuring unit 36 is supported by a bracket 38.

Figure 4:
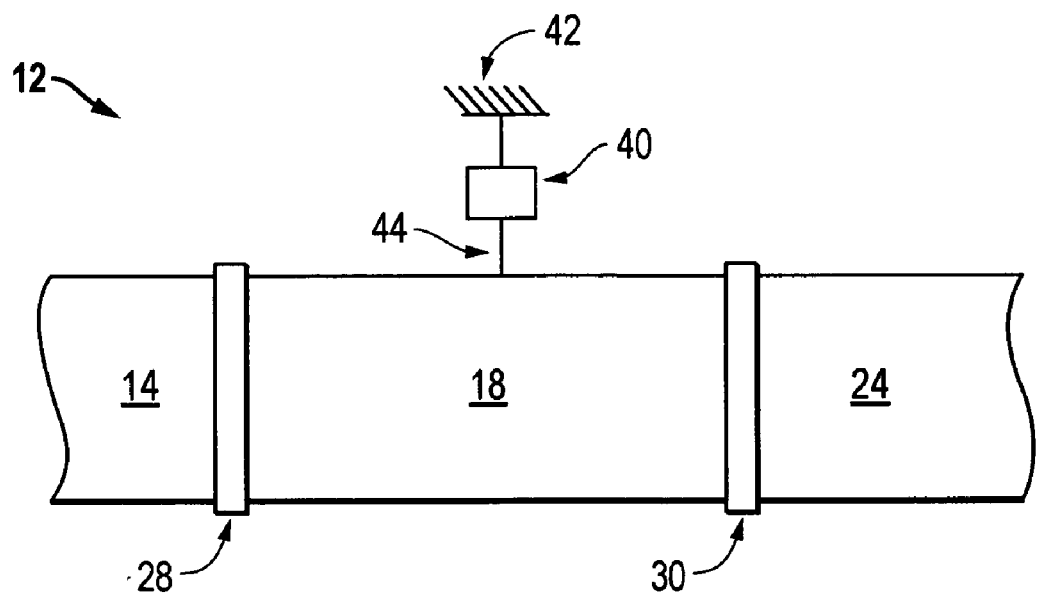
FIG. 4 is a schematic side view of a pipeline incorporating an alternate embodiment of the invention in which the weight measuring unit is installed above the densimeter rather than below the densimeter.

FIG. 4 illustrates an alternate embodiment of the density measuring apparatus. In this alternate embodiment, weight measuring unit 40 is positioned above, rather than below, the second section 18. Weight measuring unit 40 is attached to a bracket 42 or other support structure located above the pipeline. In one embodiment, weight measuring unit 40 is a tension-type load cell, such as the LCH series manufactured by Omega Engineering. As discussed above, other types of weight measuring units may be used without departing from the scope of the invention. Weight measuring unit 40 is attached to second section 18 by a support rod 44. The support rod 44, which carries the weight of the second section 18, may be connected to second section 18 by any means known to the art.

As can be best seen in FIG. 3, the densimeter 12 has an outer surface 46 and an inner surface 48. The inner surface 48 defines a bore 50 through which fluid can flow. As shown in FIG. 3, the bore 50 has a circular shape as is commonly known in the art. In a preferred embodiment of the present invention, inlet section 14, second section 18, and outlet section 24 all have the same cross-sectional shape, which matches that of the pipeline generally. This cross-sectional shape is uniform and does not vary along the length of the densimeter 12. Although the densimeter of the preferred embodiment has a uniform, circular bore, the densimeter would function equally well with any type of cross-section known to the art, such as a non-circular cross-section, an open U-tube that carries the entire flow volume, or a cross-sectional shape that varies along the length of the densimeter 12. The density measuring apparatus of the present invention can therefore be adapted for use with any type of pipeline known to the art.

The operation of the density measuring apparatus of the invention will now be described in detail. In operation, the densimeter 12 is initially empty of fluid. While the densimeter 12 is empty, the weight measuring unit 36 is calibrated to produce a reading of zero. After the weight measuring unit 36 is calibrated, a fluid of known density, such as water, is pumped through the densimeter 12 at a known flow rate. The weight measuring unit 36 is again calibrated to produce a reading of zero, while the flow rate of water through the densimeter 12 is maintained at a constant level. After the weight measuring unit 36 is calibrated to zero with a constant flow of water through the densimeter 12, other components, such as proppants or cement powder, are introduced into the water in desired proportions, resulting in a slurry. The slurry components may be any type known in the art, having a density different from that of water. Due to the different densities of the slurry components, the density of the resulting slurry will vary depending on the amount of each component present in the slurry.

The slurry flows through the pipeline in the direction indicated by the arrows in FIG. 1. The slurry flows first through the densimeter inlet section 14. When the slurry reaches the downstream end 16 of the inlet section 14, the slurry passes into the second section 18. The slurry continues to flow from the upstream end 20 of the second section 18 to the downstream end 22 of the second section 18. When the slurry reaches the downstream end 22 of the second section 18, the slurry passes into the outlet section 24. The slurry enters the upstream end 26 of the outlet section 24, flows through the outlet section 24, and continues through the pipeline.

Inlet support 32 and outlet support 34 constrain the inlet section 14 and outlet section 24 from movement in the vertical direction during slurry flow. The first flexible coupling 28 and the second flexible coupling 30 allow the second section 18 to undergo a limited amount of radial movement relative to the inlet section 14 and outlet section 24 during slurry flow.

Although the weight measuring unit 36 carries the entire weight of the second section 18 and the slurry that flows therethrough in the preferred embodiment, other configurations are possible. For example, a portion of the weight of the second section 18 may be carried by the inlet section 14, by the outlet section 24, or by any other support structure as is commonly known. Other possible configurations may also include using multiple weight measuring units; for example, one weight measuring unit may be positioned near the upstream end 20 of the second section 18 with a second weight measuring unit (not shown) positioned near the downstream end 22 of the second section 18. The density measuring apparatus of the present invention will work equally well in any of these configurations, once the weight measuring unit 36 is calibrated as described above.

Continuing with the description of the preferred embodiment, the weight of the second section 18 will change as the density of the slurry changes. For example, in the case of a slurry containing a proppant having a density greater than that of water, the density of the slurry will increase as the amount of proppant in the slurry increases. As the density of the slurry increases, the weight of the second section 18 will also increase. The flexible couplings 28, 30 enable the second section 18 to move in a radial direction independently from the inlet section 14 and outlet section 24. This independent movement of the second section 18 in turn enables the weight measuring unit 36 to register the changing weight of the second section 18. The weight measuring unit 36 is connected to a control unit (not shown) to continuously meter the weight of the second section 18 and, based on the weight of the second section 18, to calculate the density of the fluid. The control unit may be of the type disclosed in U.S. Pat. No. 6,007,227, incorporated herein by reference.

Figure 5:
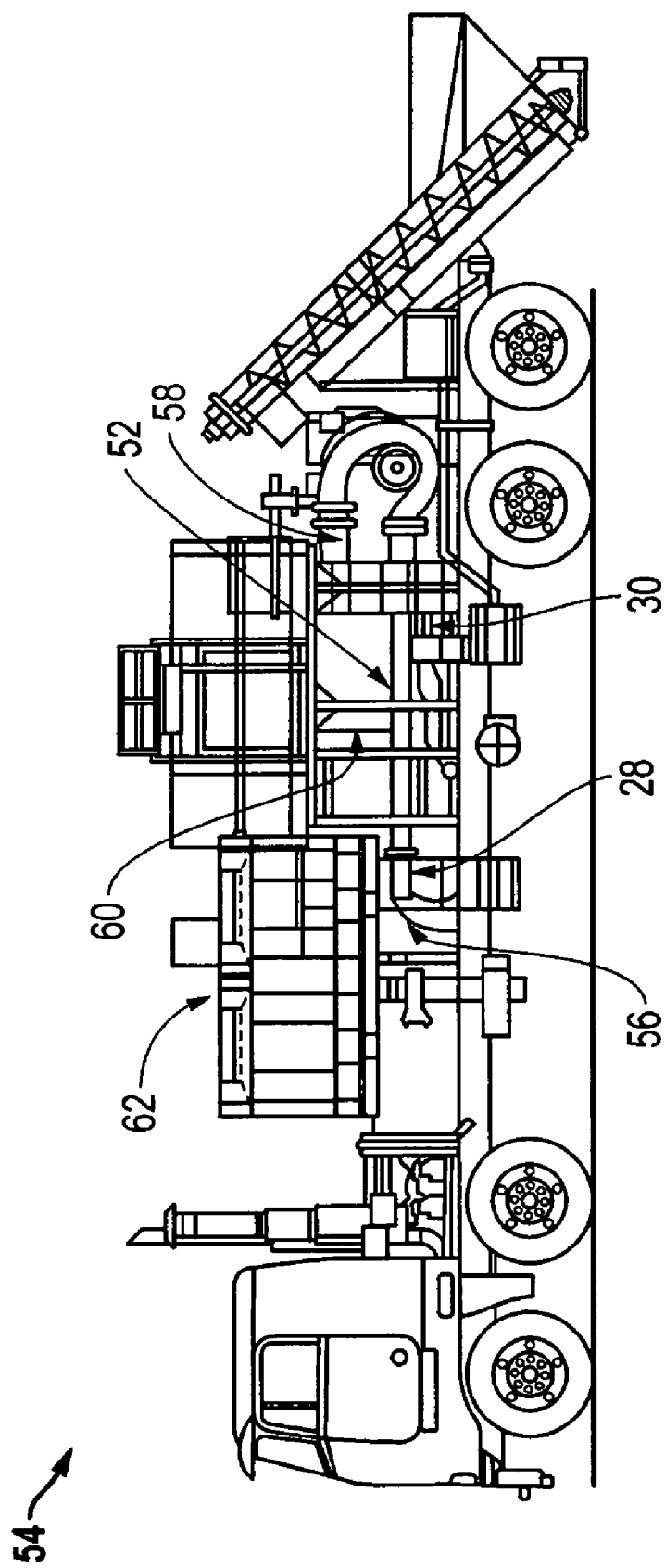
FIG. 5 is a side view of a blender truck system incorporating the density measuring apparatus of the invention.
Figure 6:
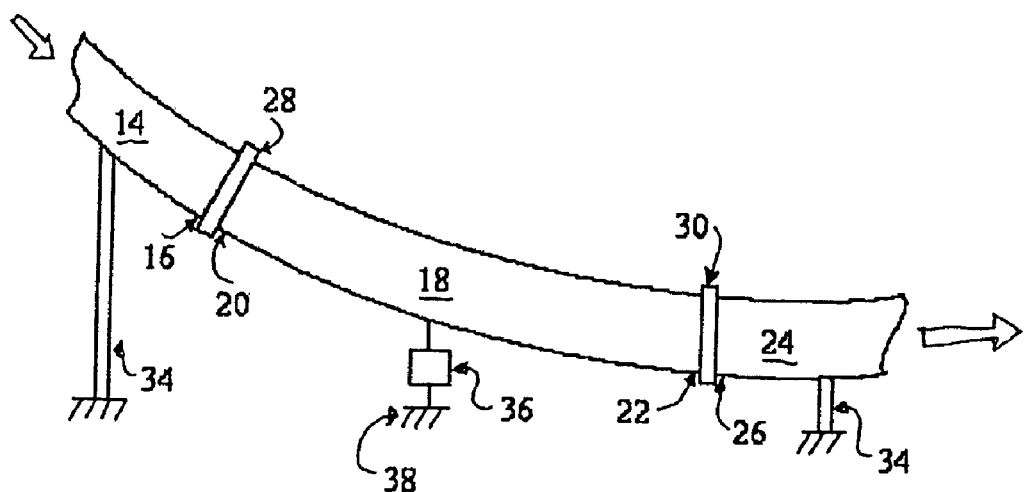
FIG. 6 is a schematic side view of a pipeline incorporating an alternate embodiment of the invention in which the longitudinal axis of the second pipe is curved from the upstream end of the second pipe to the downstream end.
Figure 7:
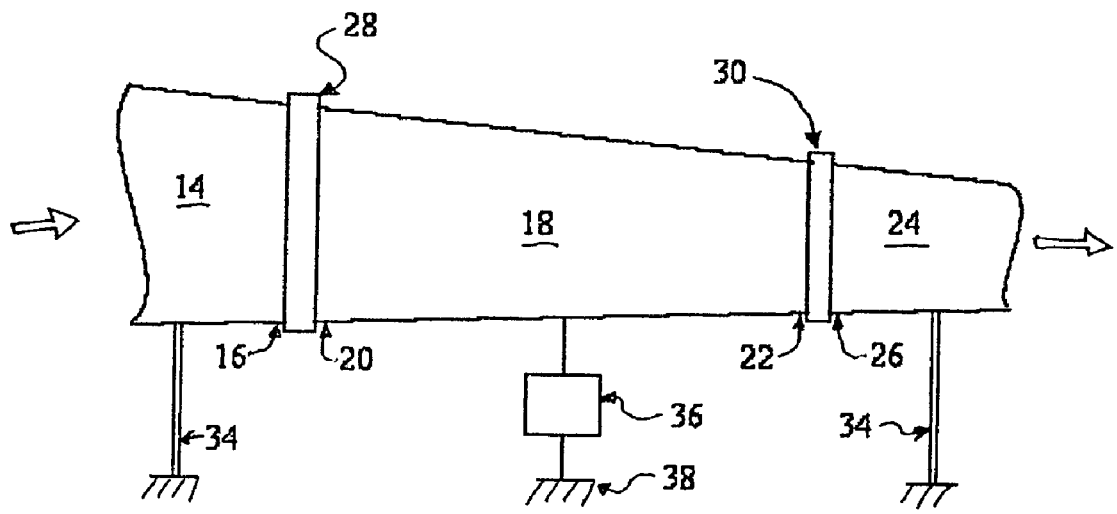
FIG. 7 is a schematic side view of a pipeline incorporating an alternate embodiment of the invention in which the cross-sectional area of the second pipe is not uniform along the length of the second pipe.

As can be seen in FIG. 5, a further preferred embodiment of the invention uses the densimeter to measure the density of a proppant in a blender system for preparing fluid mixtures for fracturing and propping oil bearing geological formations. In this preferred embodiment, flexible couplings 28, 30 join the discharge manifold 52 of a blender truck 54 to the immediately adjacent upstream section of pipe 56 and downstream section of pipe 58. The discharge manifold 52 therefore acts as the densimeter second section 18 in the above discussion. A weight measuring unit 60 is installed on the blender truck 54 underneath the discharge manifold 52 to continuously measure the weight of the discharge manifold 52. Alternatively, weight measuring unit 60 can be installed on the blender truck 54 above the discharge manifold 52.

The weight measuring unit 60 is calibrated as described above, by first measuring the empty weight of the discharge manifold 52, zeroing out the weight measuring unit 60, flowing a continuous stream of water through the discharge manifold 52, and zeroing out the weight measuring unit 60 again. Once the weight measuring unit 60 is calibrated, the blender tub 62 begins mixing a proppant into the water stream to create a slurry. The slurry leaves the blender tub 62 and flows through the discharge manifold 52, at which point it is discharged from the blender truck 54. As the slurry flows through the system, weight measuring unit 60 continuously measures the weight of the discharge manifold 52 containing the slurry. Weight changes in the discharge manifold 52 can indicate problems with the slurry composition; for example, if the proppant flow is obstructed, the slurry will contain too little proppant, resulting in a lower density slurry.

While the invention has been described with reference to a specific illustrative embodiment for use in a blender system, the present invention will also be useful in a wide range of applications wherein it is desirable to determine the properties of a variable-density substance. Therefore, the preferred embodiment showing the densimeter of the present invention used in a blender system is understood to be illustrative and not limiting.

What is claimed is:

1. A system for verifying an oil or gas well fluid mixture, comprising:
   a mixing unit adapted to create the well fluid mixture from at least two components in prescribed ratio, the fluid mixture having a target density;
   a densimeter having a first end and a second end, the second end of the densimeter being located a selected distance downstream from the first end of the densimeter, the densimeter having a bore for the flow of the fluid mixture;
   a weight measuring device capable of measuring the weight of the densimeter as the fluid mixture passes there through without appreciable time delay;
   an inlet conduit establishing fluid communication between the mixing unit and the densimeter;
   a first flexible connector coupling the first end of the densimeter to a portion of the inlet conduit so that the first end of the densimeter can move relative to the inlet conduit;
   a second flexible connector coupling the second end of the densimeter to an outlet conduit so that the second end of the densimeter can move relative to the outlet conduit;
   a control unit adapted to calculate the density of the fluid mixture flowing through the densimeter based on the weight of the fluid mixture in the densimeter and adapted to compare the calculated density with the target fluid mixture density; and
   wherein the ratio of components in the mixing unit can be varied to make the calculated density more closely match the target density thereby verifying the fluid mixture for use in an oil or gas well.

2. The system of claim 1, wherein the weight measuring device is positioned below the densimeter and is capable of supporting the weight of the densimeter.

3. The system of claim 2, wherein the weight measuring device comprises at least one compression-type load cell.

4. The system of claim 1, wherein the weight measuring device is positioned above the densimeter and is capable of supporting the weight of the densimeter.

5. The system of claim 1, wherein the weight measuring device comprises at least one tension-type load cell.

6. The system of claim 1, wherein the densimeter extends in a non-vertical direction.

7. The system of claim 1, wherein a longitudinal axis of the densimeter is substantially straight from the first end of the densimeter to the second end.

8. The system of claim 1, wherein a cross-sectional area of the densimeter is uniform for the entire length of the densimeter extending from the first end to the second end.

9. The system of claim 1, wherein the fluid mixture comprises a proppant slurry and has a target density greater than approximately the density of water.

10. The system of claim 1, wherein the fluid mixture comprises a cement slurry and has a target density greater than approximately the density of water.

11. A method of preparing a fluid mixture for use in an oil or gas well before the fluid mixture is pumped into the well, comprising:
   flowing a first fluid having a known density through a pipeline;
   calibrating a weight measuring unit that is capable of measuring the weight of a selected section of the pipeline as the first fluid flows through the selected section of the pipeline;
   creating a fluid mixture for an oil or gas well having a desired density resulting from a prescribed ratio of mixture components;
   flowing through the pipeline the fluid mixture;
   measuring the weight of the selected section of the pipeline as the fluid mixture flows through the selected section without an appreciable time delay;
   determining the density of the fluid mixture as the fluid mixture flows through the selected section of the pipeline; and
   comparing the determined density with the desired density to verify the preparation of the fluid mixture.

12. The method of claim 11, wherein the density of the fluid mixture is determined while the fluid mixture is in a process pipe on a shipping vessel.

13. The method of claim 12, wherein the shipping vessel is a truck.

14. The method of claim 11, wherein the fluid mixture comprises a proppant slurry and has a desired density greater than approximately the density of water.

15. The method of claim 11, wherein the fluid mixture comprises a cement slurry and has a desired density greater than approximately the density of water.

16. The method of claim 11, wherein comparing the determined density to the desired density is done by a control system.

17. The method of claim 16, wherein the control system continuously measures the density of the fluid mixture as the fluid mixture flows through the densimeter.

18. The method of claim 11, further comprising adjusting the ratio of components of the mixture while creating the mixture based on the comparison of the determined density to the desired density.

* * * * *